US012718920B2

(12) United States Patent
Longo et al.

(10) Patent No.: US 12,718,920 B2
(45) Date of Patent: Aug. 25, 2026

(54) DYNAMIC USER INTERFACE FOR AUTOMATED GENERATION OF CUSTOM PHYSICAL LABELS

(71) Applicant: Express Scripts Strategic Development, Inc., St. Louis, MO (US)

(72) Inventors: Karen A Longo, Pittsburgh, PA (US); Roberto A. Camara Acajabon, Corova, TN (US); Raja Sekhar Chennam, Collierville, TN (US); Chaitra Talanki, Carlsbad, CA (US); Rahul Reddy Gouravaram, Memphis, TN (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 105 days.

(21) Appl. No.: 18/543,514

(22) Filed: Dec. 18, 2023

(65) Prior Publication Data

US 2024/0120056 A1 Apr. 11, 2024

Related U.S. Application Data

(63) Continuation of application No. 16/936,930, filed on Jul. 23, 2020, now Pat. No. 11,848,084.

(51) Int. Cl.

| | |
|---|---|
| ***G16H 20/10*** | (2018.01) |
| ***G06F 16/9538*** | (2019.01) |
| ***G06F 16/958*** | (2019.01) |

(52) U.S. Cl.

CPC ......... *G16H 20/10* (2018.01); *G06F 16/9538* (2019.01); *G06F 16/958* (2019.01)

(58) Field of Classification Search

CPC .... G16H 20/10; G06F 16/958; G06F 16/9538

See application file for complete search history.

(56) References Cited

U.S. PATENT DOCUMENTS

| | | |
|---|---|---|
| 5,765,159 A | 6/1998 | Srinivasan |
| 5,883,370 A | 3/1999 | Walker |

(Continued)

OTHER PUBLICATIONS

Karystianis et al., "Modelling and extraction of variability in free-text medication presorptions from an anonymised primary care electronic medical record research database," 2016, BMC Medical Informatics and Decision Making, pp. 1-10 (Year: 2016).*

*Primary Examiner* — Kenneth Bartley

(74) *Attorney, Agent, or Firm* — Miller Johnson

(57) ABSTRACT

A computer system includes memory hardware configured to store instructions and a database, and processor hardware configured to execute the instructions. The instructions include receiving input from a user. The instructions include querying the database to: obtain a label text associated with a specified national drug code (NDC), obtain a field associated with the label text, and obtain a set of field options associated with the field. The instructions include building a data structure including the label text, the field, and the set of field options. The instructions include converting the data structure to a dynamic web interface for displaying the label text, the field, and the set of field options. The instructions include receiving a user selection of a field option of the set of field options, updating the field to reflect the user selection, and generating a label by printing the label text including the updated field.

16 Claims, 9 Drawing Sheets

(56) References Cited

U.S. PATENT DOCUMENTS

| | | | | |
|---|---|---|---|---|
| 7,493,263 | B2 * | 2/2009 | Helmus | G06Q 30/0283 700/231 |
| 7,849,398 | B2 | 12/2010 | Dabet | |
| 8,055,512 | B1 | 11/2011 | Pankow | |
| 8,180,653 | B2 | 5/2012 | Banfield | |
| 8,762,176 | B2 | 6/2014 | Banfield | |
| 9,501,615 | B2 | 11/2016 | Eletreby | |
| 10,311,977 | B2 | 6/2019 | Huff | |
| 11,011,259 | B2 | 5/2021 | Akinwale | |
| 11,017,352 | B2 | 5/2021 | Macdonald | |
| 11,163,542 | B2 | 11/2021 | Sullivan | |
| 2003/0105683 | A1 * | 6/2003 | Fratarcangeli | G06Q 10/10 705/26.1 |
| 2003/0216831 | A1 | 11/2003 | Hart | |
| 2003/0225595 | A1 | 12/2003 | Helmus | |
| 2004/0054639 | A1 | 3/2004 | Francis, Jr. | |
| 2004/0111277 | A1 | 6/2004 | Pearson | |
| 2004/0215486 | A1 | 10/2004 | Braverman | |
| 2006/0015518 | A1 | 1/2006 | Eletreby | |
| 2006/0156216 | A1 * | 7/2006 | Chen | G06F 40/174 715/205 |
| 2006/0167719 | A1 | 7/2006 | Kim | |
| 2007/0164096 | A1 * | 7/2007 | Banfield | G16H 20/13 235/375 |
| 2007/0168228 | A1 * | 7/2007 | Lawless | G06Q 40/08 600/300 |
| 2008/0042423 | A1 | 2/2008 | Roberts | |
| 2008/0059228 | A1 | 3/2008 | Bossi | |
| 2008/0103832 | A1 | 5/2008 | Hasan | |
| 2008/0306769 | A1 * | 12/2008 | Roberts | G16H 20/10 705/3 |
| 2009/0012813 | A1 * | 1/2009 | Berzansky | G16H 20/13 705/2 |
| 2009/0099870 | A1 * | 4/2009 | Wilkinson | G06F 40/274 705/3 |
| 2009/0281835 | A1 * | 11/2009 | Patwardhan | G16H 20/10 715/224 |
| 2009/0287992 | A1 | 11/2009 | Bresolin | |
| 2010/0241446 | A1 | 9/2010 | Eckert | |
| 2011/0029321 | A1 * | 2/2011 | Rourke | G06Q 40/08 707/769 |
| 2012/0016687 | A1 | 1/2012 | Dhavle | |
| 2012/0215554 | A1 | 8/2012 | Yurkovich | |
| 2012/0239463 | A1 | 9/2012 | Wertz | |
| 2013/0090947 | A1 | 4/2013 | Nockley | |
| 2013/0179177 | A1 | 7/2013 | Dhavle | |
| 2014/0188502 | A1 * | 7/2014 | Defrank | G16H 40/67 705/2 |
| 2014/0240725 | A1 | 8/2014 | Banfield | |
| 2015/0058182 | A1 | 2/2015 | Kress-Spatz | |
| 2016/0055317 | A1 | 2/2016 | Levine | |
| 2016/0210437 | A1 * | 7/2016 | Padmani | G16H 40/20 |
| 2016/0357919 | A1 | 12/2016 | Bojorquez | |
| 2017/0039346 | A1 | 2/2017 | Strader | |
| 2018/0075212 | A1 * | 3/2018 | Kubey | G06Q 10/087 |
| 2018/0366215 | A1 | 12/2018 | Tribble | |
| 2019/0026082 | A1 | 1/2019 | Shalev | |
| 2019/0279772 | A1 | 9/2019 | Huff | |
| 2021/0158413 | A1 | 5/2021 | Kello | |
| 2022/0165399 | A1 | 5/2022 | Ho | |

* cited by examiner

DYNAMIC USER INTERFACE FOR AUTOMATED GENERATION OF CUSTOM PHYSICAL LABELS

CROSS-REFERENCE TO RELATED APPLICATIONS

This application is a continuation of U.S. patent application Ser. No. 16/936,930 filed Jul. 23, 2020, the entire disclosure of which is incorporated by reference.

FIELD

The present disclosure relates to computer-automated generation of physical labels and more particularly to on-demand generation of physical labels for medication containers.

BACKGROUND

Part of dispensing a prescription drug (also referred to as an "Rx") is preparing sig text for the Rx, where "sig" is short for signa, which means "label" in Latin. The sig text is directions for the patient to determine how to take the Rx. The sig text is included on one or more of a label affixed to a container for the Rx, packaging materials, an instruction sheet, etc., and referred to for simplicity in this disclosure as a label. In the conventional approach to preparing the sig text label, a pharmacist must type free text to provide all directions for the whole sig text label. In some cases, a quick code may be selected to populate certain parts of the sig text label, such as selecting "QID" (an abbreviation of the Latin phrase meaning four times a day) to indicate taking a drug four times a day.

Other approaches may use a C-agent tool that builds the sig text label via selection from a list of many options, or allows for selection from a list of "common" sigs that have been previously prepared for the drug. A user may then edit the selected sig using free text editing. The above approaches have many disadvantages, such as increased time for the user (such as a pharmacist) to type out the full sig text label or select from hundreds of label options, possibilities for human error such as typographical errors or use of unapproved verbiage (for example, "tab" instead of "tablet," "subcutaneous" instead of "under the skin," etc.), requirements for redundant entry where the user must first type out a sig text label for printing and affixing to a bottle and then subsequently type out the sig text label a second time to record the prescription in a database for reporting purposes, etc.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A computer system includes memory configured to store computer-executable instructions and a database. The database includes a label text table configured to store multiple label texts each associated with a national drug code (NDC), a fields table configured to store multiple fields each associated with a label text, and a field options table configured to store multiple field option values each associated with a field. The system includes at least one processor configured to execute the instructions. The instructions include receiving drug input from a user, the input indicative of a specified NDC, querying the database to obtain at least one label text associated with the specified NDC, at least one field associated with the obtained label text, and multiple field options associated with the obtained field, building a data structure including the obtained label text, the obtained field, and the multiple obtained field options, and converting the data structure to a user interface for displaying the obtained label text, the obtained field, and the multiple obtained field options. The field is editable by the user to select one of the multiple obtained field options. The method includes receiving a user selection of one of the multiple obtained field options and updating the field to display the user selection, and printing the label text including the selected field to a label and/or saving the label text including the selected field to a record database.

In other features, converting the data structure to the user interface includes performing an HTML, conversion on the data structure to generate a dynamic web content user interface. In other features, the instructions include obtaining a text box field associated with the obtained at least one label text from the database query, receiving a user text entry to the text box field, and updating the text box field to display the user text entry within the displayed label text.

In other features, the instructions include obtaining a calculated field associated with the obtained at least one label text from the database query. The calculated field includes at least one calculation algorithm. In response to receiving the user text entry to the text box field or receiving the user selection of one of the multiple obtained field options, the instructions include performing the calculation algorithm to determine a value of the calculated field based on the user text entry and/or the user selection.

In other features, the instructions include obtaining a field validation rule associated with the text box field from the database query. The field validation rule specifies one or more allowable values for the text box field. The instructions include determining whether the user text entry to the text box field satisfies the field validation rule, and in response to a determination that the user text entry does not satisfy the field validation rule, displaying an error message and requesting a new text entry from the user.

In other features, querying the database to obtain at least one label text associated with the specified NDC includes obtaining multiple label texts associated with the specified NDC, and the instructions include displaying the multiple label texts associated with the specified NDC to the user, obtaining a user selection of one of the multiple displayed label texts, and receiving user input to edit the selected one of the multiple displayed label texts.

In other features, the instructions include obtaining a hidden field associated with the obtained at least one label text from the database query, incorporating the hidden field in the data structure without displaying the hidden field in the user interface, and storing a value of the hidden field in the label text when the label text is saved to the record database. In other features, the multiple field options include at least one of a dose option, a dosage unit option, and a frequency option.

In other features, receiving a user selection of one of the multiple obtained field options includes displaying the multiple obtained field options as items in a drop-down menu of the user interface, and receiving a user selection of one of the items of the drop-down menu. In other features, the instructions include displaying a text entry box adjacent the obtained label text in the user interface, receiving a user text entry to the text entry box, and updating the displayed label text to include the user text entry to the text entry box.

In other features, a computerized method includes receiving drug input from a user, the input indicative of a specified NDC, and querying a database to obtain at least one label text associated with the specified NDC, at least one field associated with the obtained label text, and multiple field options associated with the obtained field. The database includes a label text table configured to store multiple label texts each associated with a national drug code (NDC), a fields table configured to store multiple fields each associated with a label text, and a field options table configured to store multiple field option values each associated with a field. The method includes building a data structure including the obtained label text, the obtained field, and the multiple obtained field options, and converting the data structure to a user interface for displaying the obtained label text, the obtained field, and the multiple obtained field options. The field is editable by the user to select one of the multiple obtained field options. The method includes receiving a user selection of one of the multiple obtained field options and updating the field to display the user selection, and printing the label text including the updated field to a label and/or saving the label text including the updated field to a record database.

In other features, converting the data structure to the user interface includes performing an HTML, conversion on the data structure to generate a dynamic web content user interface. In other features, the computerized method includes obtaining a text box field associated with the obtained at least one label text from the database query, receiving a user text entry to the text box field, and updating the text box field to display the user text entry within the displayed label text.

In other features, the computerized method includes obtaining a calculated field associated with the obtained at least one label text from the database query. The calculated field includes at least one calculation algorithm. In response to receiving the user text entry to the text box field or receiving the user selection of one of the multiple obtained field options, the method includes performing the calculation algorithm to determine a value of the calculated field based on the user text entry and/or the user selection.

In other features, the computerized method includes obtaining a field validation rule associated with the text box field from the database query. The field validation rule specifies one or more allowable values for the text box field. The method includes determining whether the user text entry to the text box field satisfies the field validation rule, and in response to a determination that the user text entry does not satisfy the field validation rule, displaying an error message and requesting a new text entry from the user.

In other features, querying the database to obtain at least one label text associated with the specified NDC includes obtaining multiple label texts associated with the specified NDC, and the method includes displaying the multiple label texts associated with the specified NDC to the user, obtaining a user selection of one of the multiple displayed label texts, and receiving user input to edit the selected one of the multiple displayed label texts.

In other features, the computerized method includes obtaining a hidden field associated with the obtained at least one label text from the database query, incorporating the hidden field in the data structure without displaying the hidden field in the user interface, and storing a value of the hidden field in the label text when the label text is saved to the record database. In other features, the multiple field options include at least one of a dose option, a dosage unit option, and a frequency option.

In other features, receiving a user selection of one of the multiple obtained field options includes displaying the multiple obtained field options as items in a drop-down menu of the user interface, and receiving a user selection of one of the items of the drop-down menu. In other features, the computerized method includes displaying a text entry box adjacent the obtained label text in the user interface, receiving a user text entry to the text entry box, and updating the displayed label text to include the user text entry to the text entry box.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

In the drawings, reference numbers may be reused to identify similar and/or identical elements.

DETAILED DESCRIPTION

High-Volume Pharmacy

Figure 1:
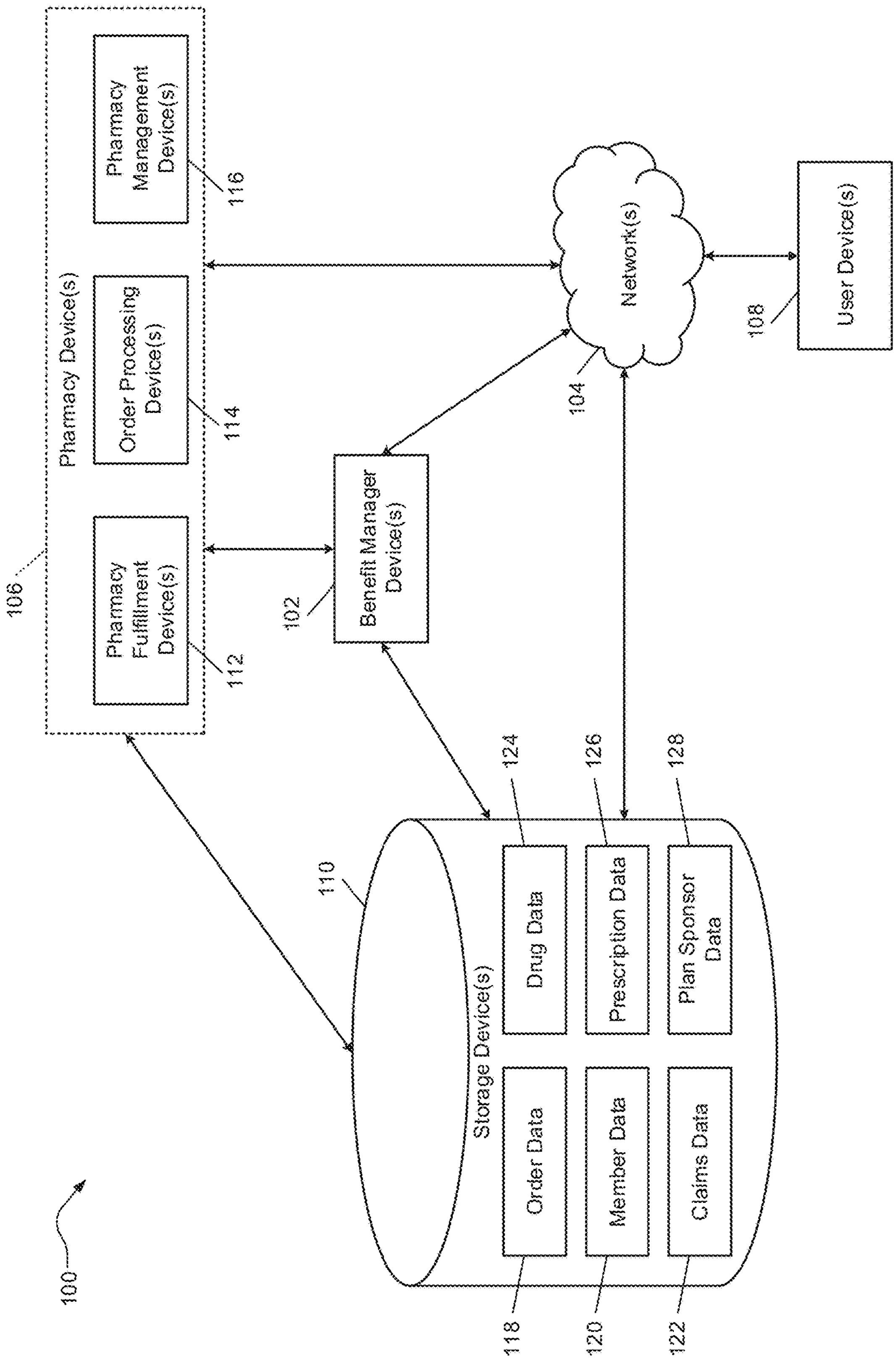
FIG. 1 is a functional block diagram of an example system including a high-volume pharmacy.

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104.

The system 100 may also include one or more user device(s) 108. A user, such as a pharmacist, patient, data analyst, health plan administrator, etc., may access the benefit manager device 102 or the pharmacy device 106 using the user device 108. The user device 108 may be a desktop computer, a laptop computer, a tablet, a smartphone, etc.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in a storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Virginia.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfillment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), etc. The drug data 124 may include information associated with a single medication or multiple medications.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Figure 2:
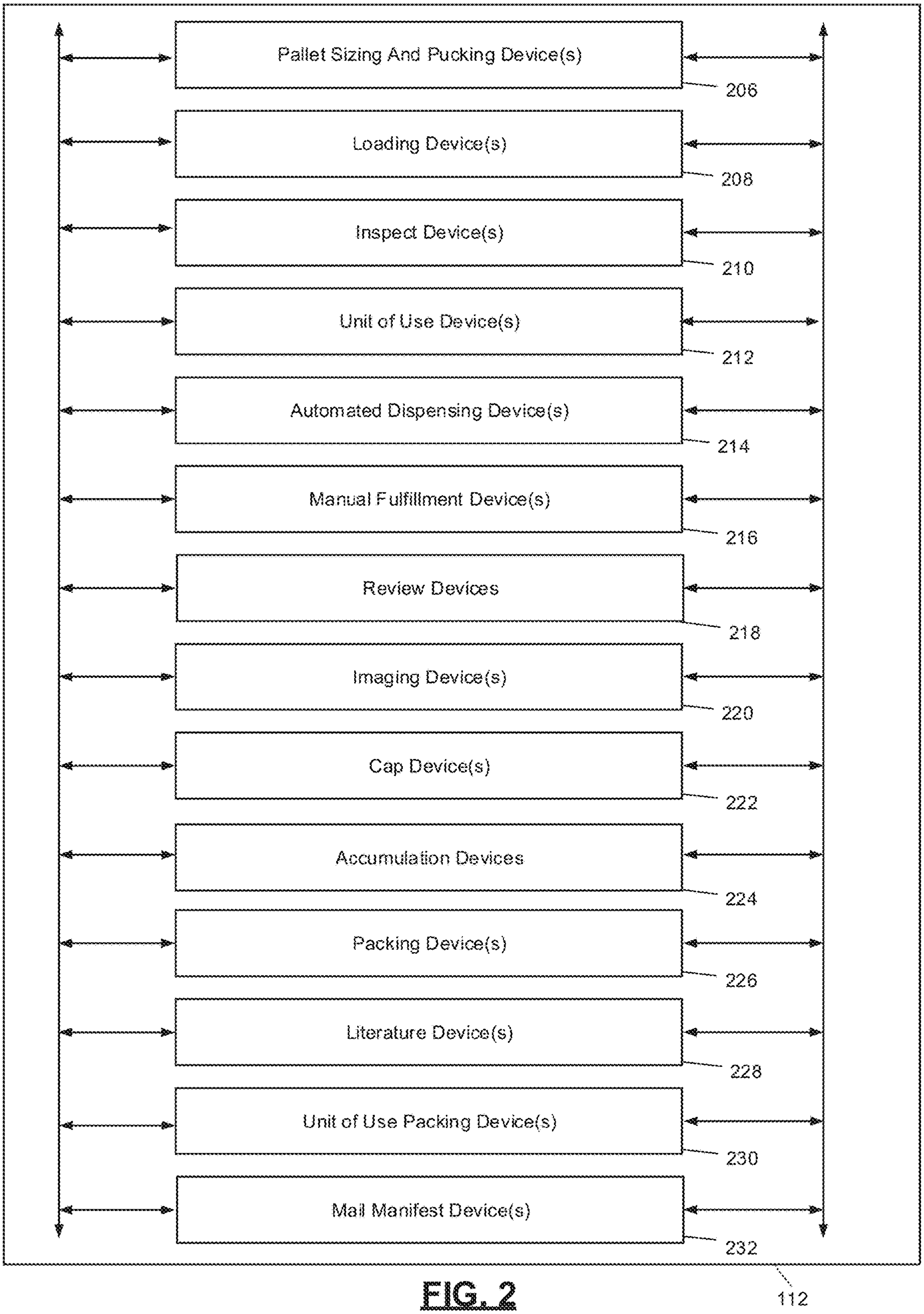
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
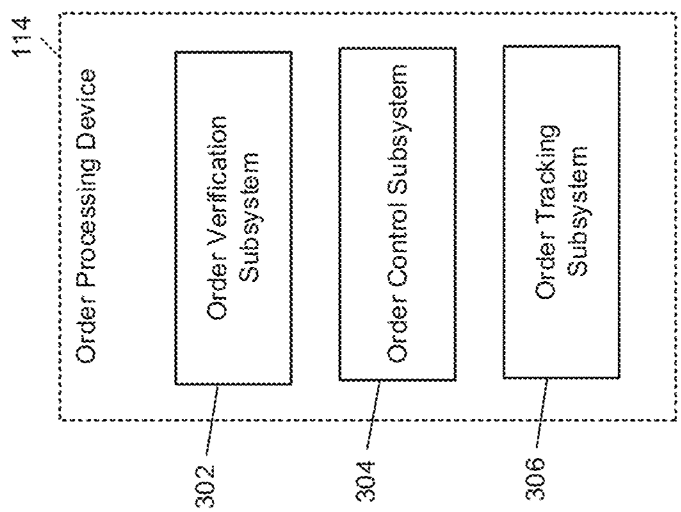
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may be comprised of order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Sig Table Database System

Part of dispensing a prescription drug (also referred to as an "Rx") is preparing sig text for the Rx, where "sig" is short for signa, which means "label" in Latin. The sig text is directions for the patient to determine how to take the Rx. The sig text is included on one or more of a label affixed to a container for the Rx, packaging materials, an instruction sheet, etc., and referred to for simplicity in this disclosure as a label. In the conventional approach to preparing the sig text label, a pharmacist must type free text to provide all directions for the whole sig text label. In some cases, a quick code may be selected to populate certain parts of the sig text label, such as selecting "QID" (an abbreviation of the Latin phrase meaning four times a day) to indicate taking a drug four times a day.

Other approaches may use a C-agent tool that builds the prescription drug (also referred to as "Rx") label via selection from a list of many options, or allows for selection from a list of "common" sigs that have been previously prepared for the drug. A user may then edit the selected sig using free text editing. The above approaches have many disadvantages, such as increased time for the user (such as a pharmacist) to type out the full sig text label or select from hundreds of label options, possibilities for human error such as typographical errors or use of unapproved verbiage (for example, "tab" instead of "tablet," "subcutaneous" instead of "under the skin," etc.), requirements for redundant entry where the user must first type out a sig text label for printing and affixing to a bottle and then subsequently type out the sig text label a second time to record the prescription in a database for reporting purposes, etc.

In various implementations described herein, a sig table database is used to assist users in building sig text label in a more efficient, accurate, and recordable manner. For example, the sig text label may store, for each NDC, one or more specific sig text labels that correspond to the NDC, one or more editable fields that each include only a small set of options that specifically correspond to the NDC, etc.

The sig text database may allow for implementation of a sig text builder that configures Rx label choices down to the national drug code (NDC) level. Instead of a list of hundreds of available frequencies that may be assigned for all possible drugs, in various implementations the list of possible frequencies may be narrowed down to only a few values that correspond to a selected NDC. For example, when a user selects a specific NDC (or selects a specific drug corresponding to an NDC), the sig text builder may display only a small number of frequency options that are possible for the specific drug that was selected, while ignoring hundreds of other frequency options that apply only to other drugs.

Providing a specific sig text label in response to a selected NDC, with a limited number of editable fields that each have only a specified number of options that correspond to the selected NDC, may increase efficiency for the user by reducing or avoiding free text entry, reducing the number of options that the user must scroll through to find a desired option corresponding to the NDC, etc. The user may simply click on one of few options that correspond to the NDC instead of having to take the time to type out a full label or review hundreds of generic options that could apply to any one of a wide range of drugs, but are not relevant to the specific NDC selected by the user.

The sig text builder may increase quality of the sig text labels by avoiding typographical errors, avoiding use of unapproved verbiage for the sig text labels, adhering to drug dispensing guidelines, etc. For example, the sig text builder may ensure that the sig text label uses the word "tablet" instead of "tab," or the phrase "under the skin" instead of "subcutaneous," to avoid short-hand or complex medical terminology that may otherwise be entered by a user to confuse a patient.

Calculations may be performed automatically for certain fields of a sig text label, to avoid mathematical errors by users. Validation rules may be applied for certain fields, to inhibit users from selecting options or entering values that exceed upper or lower boundaries for a specified NDC, are outside of an acceptable range, etc.

In various implementations, common sig text labels may be provided for specific NDCs. For example, if an NDC frequently uses the same sig text label in ninety percent of cases, the common sig text label may be provided to the user as a starting point option in the sig builder. The common sig text label may be editable by a user in specified fields, while other portions of the common sig text label are non-modifiable (e.g., open editing or free-texting may be prevented).

Because the Rx label is systematically broken down into different data fields, the data fields may be used for pharmaceutical reporting, internal reporting, etc. For example, when the completed sig text label is saved to a record database, the record database may be searched to identify common prescription values by NDC for clinical purposes, for drug manufacturer purposes, etc. And as mentioned above, the sig text builder may avoid redundant data entry by the user, because fields such as dose, dosage unit, frequency, etc. are already known in the sig text label for data recording and reporting purposes.

Figure 4:
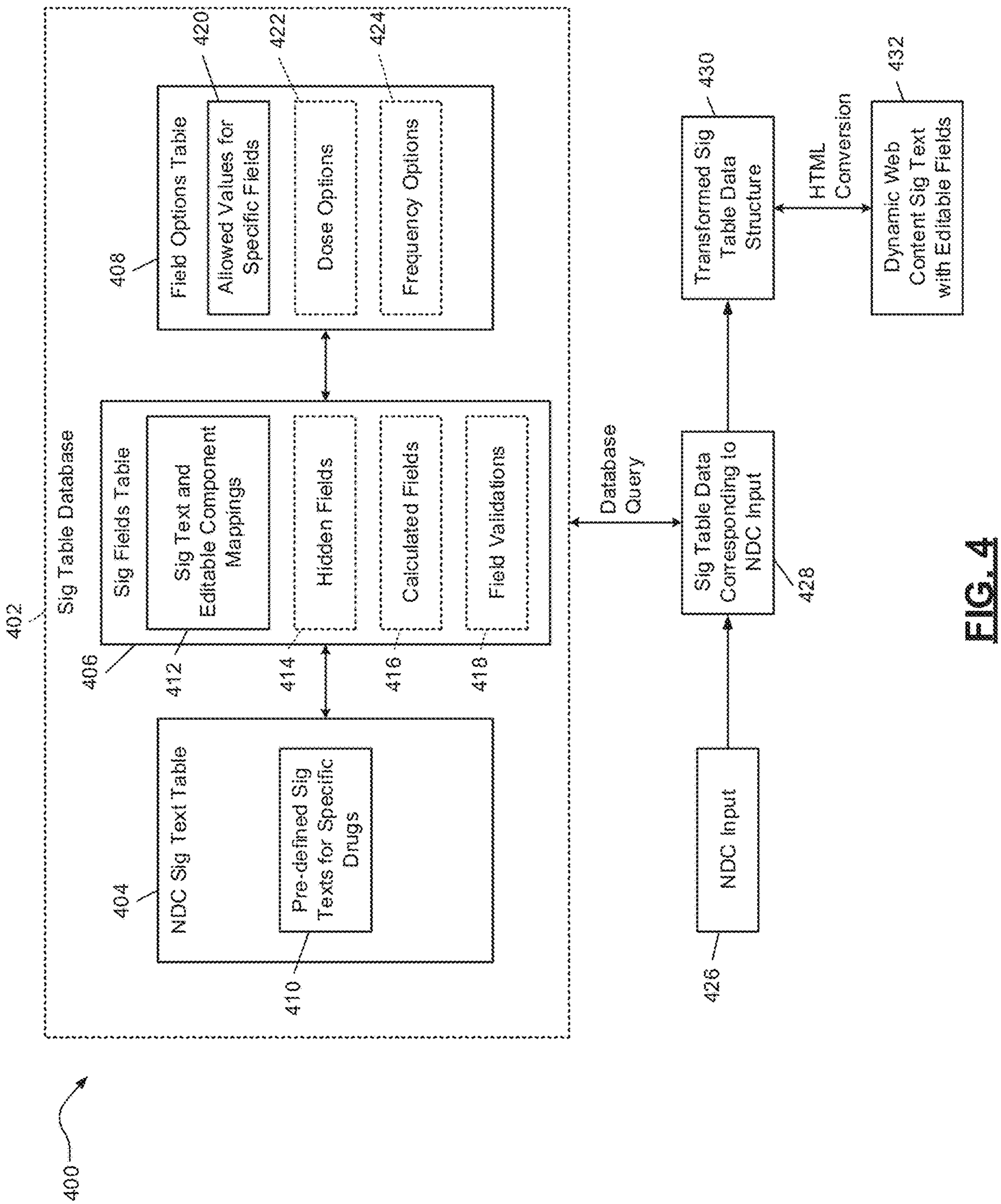
FIG. 4 is a functional block diagram of an example sig text builder system, including a sig table database.

FIG. 4 illustrates an example sig text builder system 400, including a database 402 (e.g., a sig table database, etc.). The database 402 may include any suitable configuration metadata, etc., such as tables that are used to configure label texts (e.g., sig texts, etc.) and corresponding variable fields for various NDCs. As shown in FIG. 4, the database 402 includes an NDC label text table 404 (e.g., a sig text table, etc.), a fields table 406 (e.g., a sig fields table, etc.), and a field options table 408. In various implementations, the tables 404, 406 and 408 may be generated by a system administrator (e.g., based on expert knowledge of ranges of typical sig texts used by pharmacists for each NDC, based on data analysis of historical sig text labels used for specific NDCs, etc.). The tables 404, 406 and 408 may be updated periodically to improve the sig builder process for a user. Although FIG. 4 illustrates the database 402 as including three tables, various implementations may include more or less tables, sig text components stored in other arrangements, etc.

The NDC label text table 404 may contain multiple pre-defined label texts 410 (e.g., sig texts, etc.) that each correspond to a different specific drug. For example, each NDC may have one or more pre-defined sig texts 410 stored in the table that specify a starting point sig text label associated with the NDC. The NDC label text table 404 may interact with the sig fields table 406 based on a number of sig fields included in each pre-defined sig text 410 (e.g., each pre-defined sig text 410 may be linked with specific fields from the sig fields table that correspond to or are included in the pre-defined sig text 410).

The sig fields table 406 includes mappings 412 of the editable components (e.g., editable fields, text boxes, drop down menus, etc.) within each sig text, for each NDC. For example, in the sig text "Take <one> tablet <daily>", the fields <one> and <daily> may be editable by the user. The mappings 412 may store the locations of these editable components within the sig text (e.g., relative to one another, relative to non-editable text, etc.). In various implementations, each pre-defined sig text 410 may be linked to a specific mapping 412 of editable components within the pre-defined sig text 410. Each sig text label may include a unique identifier (SIG_ID) that is mapped to a specific NDC, where each field in the sig text label includes a unique field identifier (FIELD_ID) that is mapped to the SIG_ID.

The sig table database 402 optionally includes hidden fields 414. The hidden fields 414 are not visible to the user when editing the sig text label, but may be calculated as the user edits other fields, may persist in the database or be sent to other external systems for processing of data, etc. The sig table database 402 optionally includes calculated fields 416, which may or may not be visible to the user during editing of the sig text label. An algorithm may calculate a value of the calculated field 416 using selections by the user as input parameters, which can accelerate the sig text label editing process and avoid human errors. For example, if the user enters a single dose amount and a frequency, a calculated field 416 may automatically display a total dosage for the drug, etc.

As shown in FIG. 4, the sig fields table 406 optionally includes field validations 418. Each defined field in the sig fields table 406 may be set to validate the input value for the field. Field validations 418 may be particularly useful for fields that allow free text entry, where users can enter any value. For example, field validations 418 may define the values that allowed to be entered in a field, such as only numeric values, values that are restricted within a range based on minimum and maximum boundaries, values that are specified as integers or allowed numbers of decimal places, etc.

During runtime, the sig text builder program may check whether any of the displayed field values has an associated field validation rule 418. If so, the validation rule may be applied to determine whether user input is acceptable. Example pseudocode for performing validation during runtime is shown here:

```
When validation exists then:
  For each validation type:
  If validation type is <<numeric values>> then:
    Apply function to identify non numeric values;
    If function finds non-numeric value then
      Return error;
```

The sig table database 402 may include a field options table 408, which may specify the values 420 that are possible or allowed for a particular field. For example, in the sig text "Take <one> tablet <daily>", the field <one> may be defined as a dose option 422, and the field <daily> may be defined as a frequency option 424. For example, the frequency options 424 may be specified as one of "daily", "weekly", and "twice a week". When a user selects a drop down for the <daily> field in the above sig text example, the frequency options 424 may specify what other available options are displayed for the user to choose from, according to the selected NDC that the sig text is based on.

The field options table 408 may be linked with fields in the sig fields table 406, where the field option values 420 are assigned to each field that is included in a sig text label for a specific NDC. For example, each field identifier (FIELD_ID) may be mapped to a field option such as doses, dosage units, frequency, etc. In various implementations, the field options table 408 may include options other than dosage and frequency.

As shown in FIG. 4, a user provides an NDC input 426 (or an NDC is identified that corresponds to a prescription drug or over-the-counter (OTC) drug selected by the user). At 428, a database query is issued to obtain data from the sig table database that corresponds to the NDC input 426. For example, the NDC input 426 be supplied to the sig table database 402 as part of the database query, and the sig table database 402 may return sig table data 428 including a pre-defined sig text 410, sig field editable component mappings 412, and field option values 420, that correspond to the NDC input 426.

The sig table data 428 is transformed into a sig table data structure 430, which may be used to generate a user interface for editing the sig text label. For example, the pre-defined sig text 410, the sig field editable component mappings 412, field option values 420, etc. that are returned from the query to the sig table database 402 may be transformed into the sig table data structure 430. Example pseudocode for generating the sig table data structure 430 is shown here:

```
For each sig text -> create a data structure;
  Get list of fields; For each field {
    Sort field;
    Get list of options;
    Get validations;
    If field is calculated, then {
      Find formula values;
      Evaluate formula and parameters;
      Execute formula; }
    }
```

The sig table data structure 430 is converted into dynamic web content 432 that the user can edit to complete the sig text label. For example, an HTML, conversion may be performed on the sig table data structure 430 to generate the dynamic web content 432 with editable fields. The predefined sig text 410, sig field editable component mappings 412, field option values 420, etc. of the sign table data structure 430 may be converted into the dynamic web content 432, to allow a user to edit the fields. Example pseudocode for converting the sig table data structure 430 to the dynamic web content 432 is shown here:

```
For each field in the sig text;
  Evaluate the field type;
  If the field type is editable, then {
    If the field contains options, then {
      Display the field as a dropdown; }
    Else {
      Display the field as a text entry area; }
    If the field has a default value, then {
      Set the default value of the field; }
    If the field has validations rule(s), then {
      Set the validation parameters for the field; }
  }
  Else {
    Display the field as text of the label;
```

The sig table database 402 may be maintained, and the database query data 428 may be transformed into the data structure 430 and converted to the dynamic web content 432, using any suitable programming languages and systems, including but not limited to Pega, JavaServer Pages (JSP), JavaScript, Hypertext Markup Language (HTML), Dynamic HTML (DHTML), CSS (Cascading Style Sheets), business rule engines (BREs), Servlets, RXP applications, etc. As an example only, an example of Pega code for dynamically generating the user interface is shown here:

```
<pega:withReference name=".PROPERTY_VALUE">
  <pega:save name="DropDownDefault" ref="$this-value" />
  <div class="esidiv">
  <select id="<pega:reference name="$this-name"/>"
  class="esidropdown">
  <pega:forEach name=".Options">
    <pega:withEmbedded name = "$this">
    <pega:when test=".OPTION_VALUE ==
    $save(DropDownDefault)">
        <option value="<p:r n=".OPTION_VALUE"/>">
          <pega:reference name = ".OPTION_DISPLAY"/>
        </option>
      </pega:when>
```

Sig Builder Process

Figure 5:
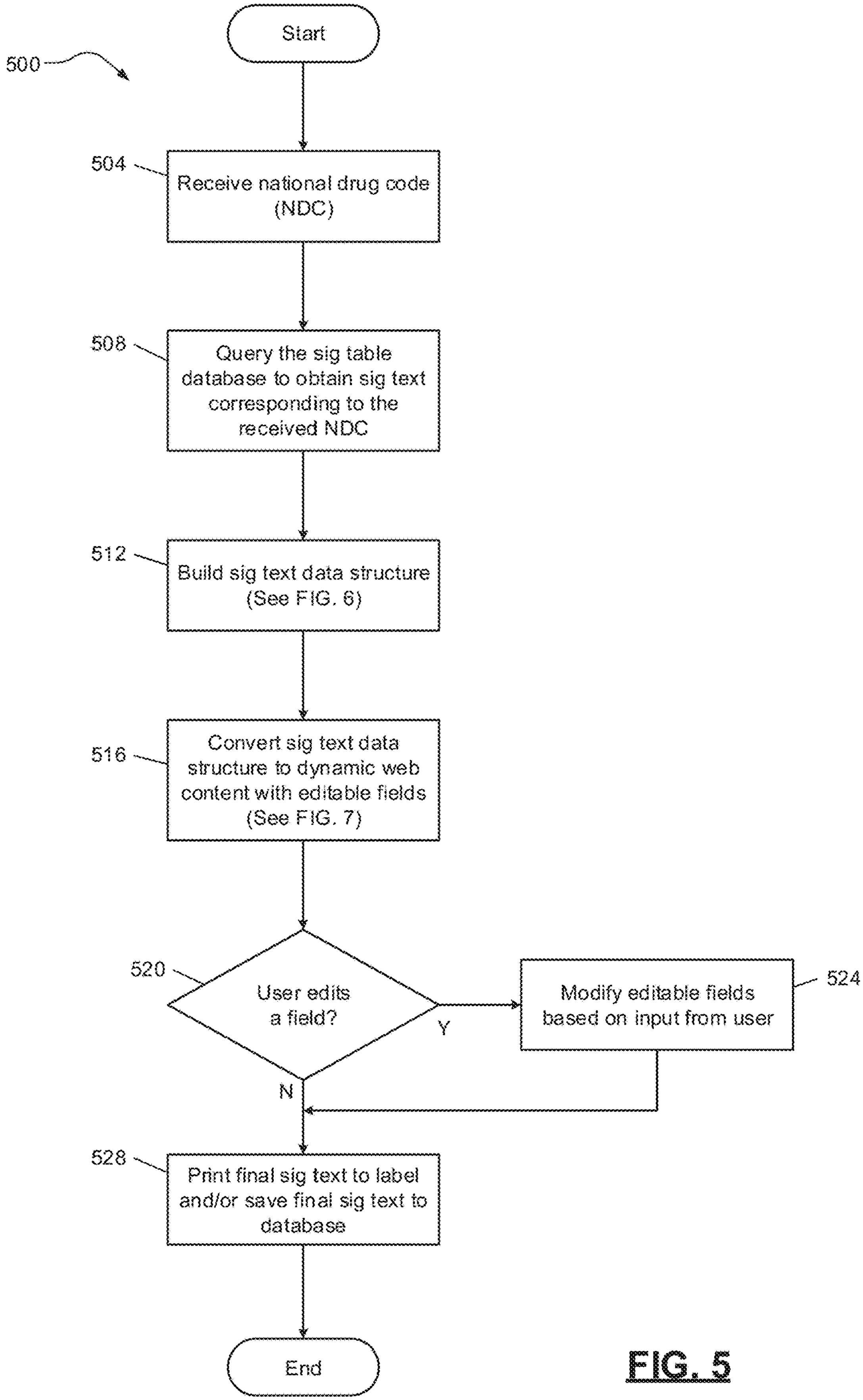
FIG. 5 is a flowchart depicting an example method of building a sig text for a specified national drug code (NDC).

FIG. 5 is a flowchart depicting an example method 500 of building a sig text for specified national drug code (NDC). Although the example method is described below with respect to the sig text builder system 400, the method may be implemented in other devices and/or systems.

In FIG. 5, control begins at 504 by receiving a national drug code (NDC). For example, a user (e.g., a pharmacist, etc.) may enter an NDC code directly, the user may enter a prescription drug by name, and control may obtain the NDC corresponding to the entered prescription drug name based on a table or database lookup, etc.

Figure 6:
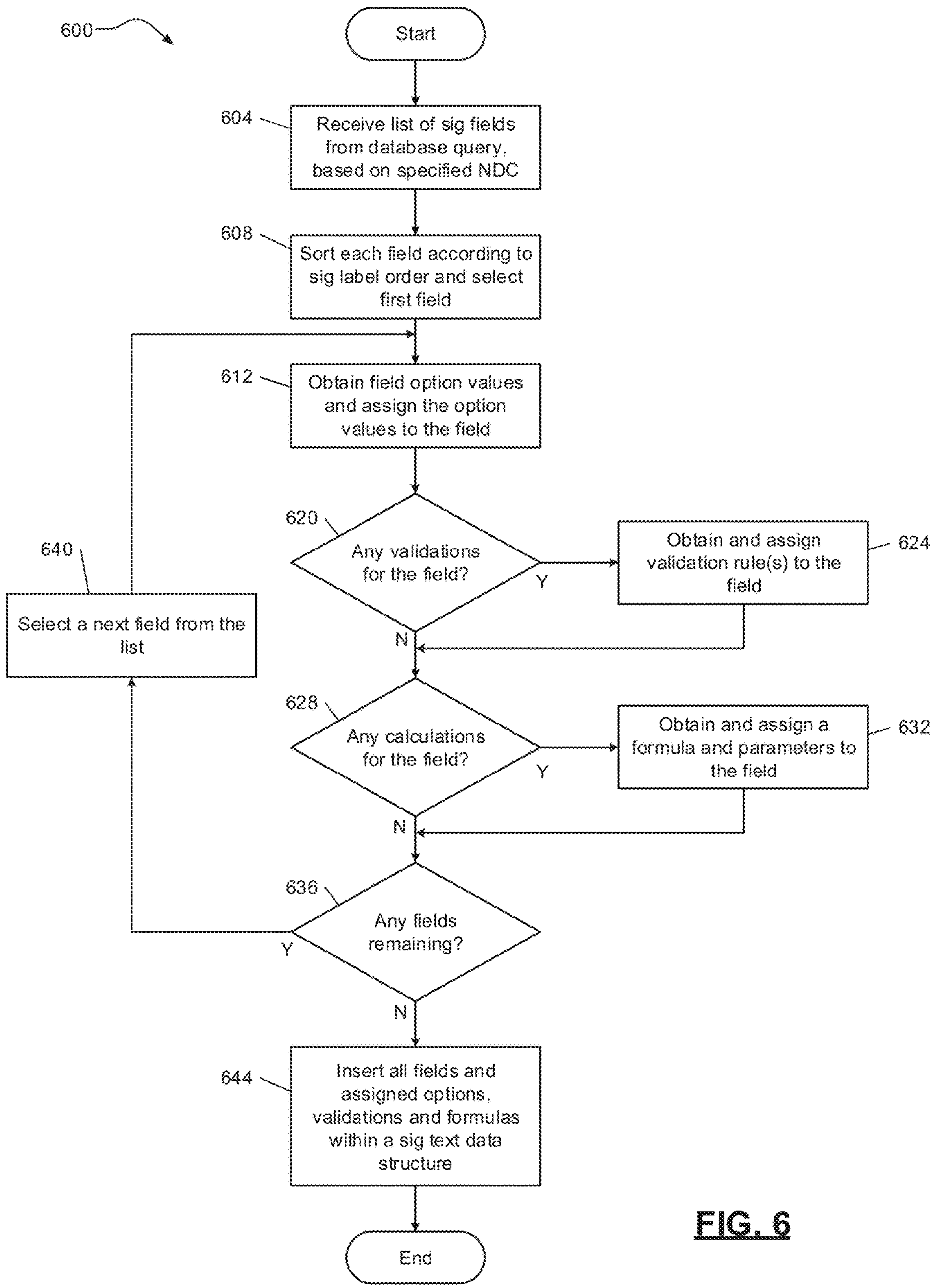
FIG. 6 is a flowchart depicting an example method of building a sig text data structure, as part of the example method of FIG. 5.
Figure 7:
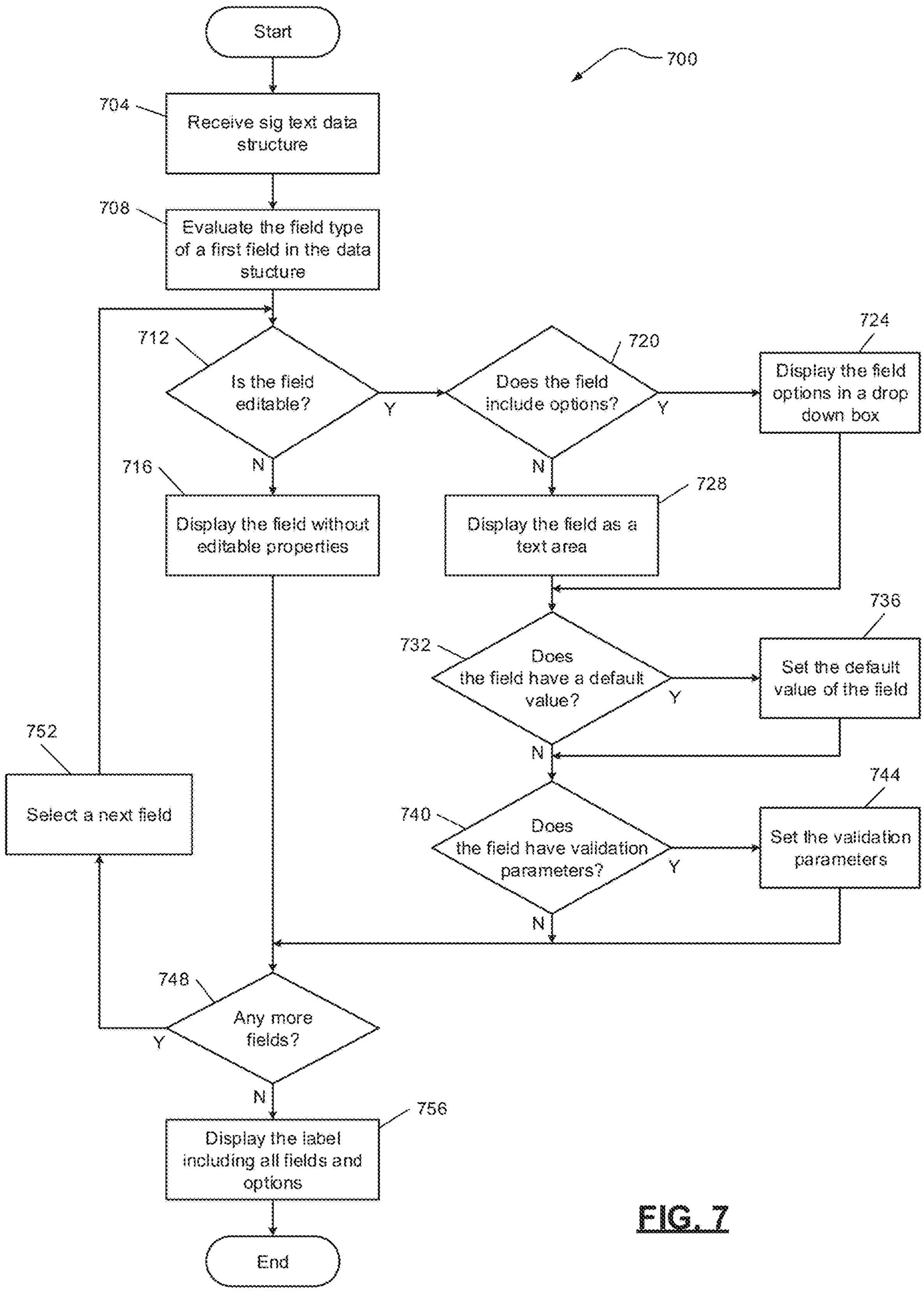
FIG. 7 is a flowchart depicting an example method of converting a sig text data structure to dynamic web content with editable fields, as part of the example method of FIG. 5.

At 508, control queries the sig table database to obtain sig text that corresponds to the received NDC. For example, control may query the sig table database 402 illustrated in FIG. 4, using the obtained NDC. After receiving the sig text corresponding to the obtained NDC, control proceeds to build a sig text data structure at 512. Further details regarding building of the sig text data structure are illustrated in FIG. 6, and described further below. Referring again to FIG. 5, control proceeds to convert the sig text data structure to dynamic web content with edible editable fields at 516. Further details of converting the sig text data structure to the dynamic web content with editable fields are illustrated in FIG. 7, and described further below.

After control converts the sig text data structure to the dynamic web content, control determines at 520 whether the user has edited a field in the dynamic web content. If so, control proceeds to 524 to modify the editable fields based on the input received from the user. For example, the user may select one of multiple values from a drop-down menu, may enter text in one or more text boxes, etc.

Once the user is finished editing the fields at 524, or if the user did not have any fields to edit at 520, control proceeds to 528 to print the final sig text to a label and/or save the final sig text to a record database. For example, once the sig text label is finalized (e.g., once the user has finished editing all fields or decided that no fields need to be edited, etc.), the finalized sig text label may be printed for applying to a container (e.g., bottle, etc.) that holds the prescription drug for providing to a customer, etc.

The final sig text label may be saved to a record database at 528, to maintain a record of the prescribed drug text. The database may be used for record-keeping as well as various other purposes. For example, fields of the saved sig text label may be used for internal monitoring, such as clinical monitoring, data aggregation of commonly prescribed values, etc. The records may be used for contact with the manufacturer, such as for determining frequencies of prescribed drug usage, etc. Saving the finalized sig text label to a record database in this manner may provide clean data without errors that could otherwise be introduced if pharmacists were required to redundantly enter all sig text again separately from the label printout each time that the drug was prescribed.

In various implementations, the final sig text may be transmitted to legacy systems to maintain consistent record keeping. For example, legacy systems may store prescription labels in specified formats, which may be traditionally entered by a pharmacist retyping the label, etc. The sig text builder may format the final sig text according to the specified legacy system format, and transmit to the legacy system for record keeping.

FIG. 6 is a flowchart depicting an example method 600 of building a sig text data structure. Although the example method is described below with respect to step 512 in the method 500 of FIG. 5, the method 600 may be implemented in other processes, devices and/or systems.

At 604, control begins by receiving a list of sig fields from a database query, based on a specified NDC. For example, the sig table database 402 may supply a list of editable fields that correspond to the NDC along with mappings of the fields within the sig text label, such as the mapping 412 in the sig fields table 406 of the sig table database 402.

At 608, control proceeds to sort each field according to its order in the sig label text, and then selects a first field in the order. For example, a sig text label may include multiple fields arranged in a particular order throughout the sig text. Control may begin by selecting the first field, and then deploying that field first within the sig text label structure.

At 612, control obtains field option values for the selected field, and assigns the option values to the field. For example, the database query to the sig table database 402 based on the NDC may have returned one or more values from the field options table 408 that correspond to the sig text for the specified NDC. The field options could include allowed values for the specific field, optional dose options 422 for the field, optional frequency options 424 for the field, etc. The options may specify the allowed frequencies, dosages, etc. that a pharmacist may select for the specified field, and control may assign these options to the field in order to build the sig text data structure appropriately.

At 620, control proceeds to determine whether there any validation rules for the selected field. For example, some fields may include field validations 418, which can be used to prevent a pharmacist from selecting a value for the field that exceeds an acceptable boundary arrange, etc. Field validations may be specified ahead of time by an administrator or creator of the sig table database 402, based on knowledge of upper and lower limits of safe or effective ranges for doses, dosage units, frequency, etc. If any validation rules are associated with the selected field at 620, control proceeds to obtain the validation rule and assigns the validation rule to the field at 624.

Once validation rules are assigned to the field at 624, or if control determines at 620 that no validation rules are associated with the field, control proceeds to 628 to determine whether any calculations are associated with the field. For example, some fields may be automatically calculated, may use values from other fields to automatically calculate total dosages, calculated frequencies, etc., which can reduce or avoid potential sources of human error. If control determines at 628 that the field is associated with a calculation (e.g., if the selected field is a calculated field 416 from the sig fields table 406, etc.), control may assign any corresponding formulas and parameters to the field at 632.

Once calculated field formulas parameters are assigned to the field at 632, or if control determines at 628 that the field is not associated with any calculations, control proceeds to 626 to determine whether any fields remain in this sig text label obtained from the database query based on the NDC. If so, control proceeds to 640 to select the next field from the list of sig text fields obtained from the database query, and returns to 612 to obtain field option values for the next selected field.

Once all selected fields have been processed, control determines at 636 that no fields are remaining and proceeds to 644 to insert all fields in the sig text data structure, including their assigned options, validations and formulas. The sig text data structure may then be used to create dynamic web content for user interaction to edit the fields, such as shown at 516 in FIG. 5.

FIG. 7 is a flowchart depicting an example method 700 of converting a sig text data structure to dynamic web content with editable fields. Although the example method is described below with respect to step 516 in the method 500 of FIG. 5, the method 700 may be implemented in other processes, devices and/or systems.

At 704, control begins by receiving the sig text data structure. For example, control may receive the sig text data structure generated according to the method 600 of FIG. 6. At 708, control evaluates the field type of first field in the data structure. Control determines at 712 whether the selected field is editable. If not, control proceeds to 716 to display the field without any editable properties (e.g., the field is displayed in the dynamic web content as text that the user is not allowed to edit, etc.).

If the selected field is editable at 712, control proceeds to 720 to determine whether the field includes field options. If the field does include assigned field options at 720, control displays the field options in a drop-down box at 724. For example, if the field includes three frequency options that the user may select from, control displays three options in a drop-down box at 724. If the field does not include any assigned options at 720, control displays the field as a text area at 728. In this case, a text box may be displayed that allows the user to enter their own text for the field.

At 732, control determines whether the field as a default value. If the field does have a default value, control proceeds to 736 to set the default value of the field. For example, if the field has a standard value that is commonly used in 95% of cases when a drug corresponding to the NDC is prescribed, the common value may be assigned as a default value of the field. The default value may be displayed at 736 as an initial value when the pharmacist views the dynamic web content. Therefore, the pharmacist may save time by avoiding entry of the common value in most cases (which may reduce on human error), while the pharmacist still has the option to change the default setting if needed.

After the default value is displayed at 736, or if control determines at 732 that the field does not have an associated default value, control proceeds to 740 to determine whether the field has validation parameters. If so, control proceeds to 744 to set the validation parameters for the field. For example, if validation rules have been assigned to the field in the sig text data structure, such as upper or lower boundaries, allowable ranges, etc., control may apply the validation rules to the field in the dynamic web content at 744. Accordingly, errors may be displayed if a user enters values that exceed one of the boundaries, are outside of the range of acceptable values, etc.

After the validation rules have been assigned to the field at 744, or if control determines at 740 that the field does not have any associated validation parameters, control proceeds to 748 to determine whether any more fields remain in the sig text data structure. If so, control proceeds to 752 select to select the next field in the sig text data structure, then returns to 712 to determine editable properties for the field. Once all fields in the sig text data structure been processed, control proceeds to 756 to display the label (including all fields and options), in a dynamic web content format that allows the user to select and/or enter the desired sig text values.

User Sig Builder Entry

Figure 8:
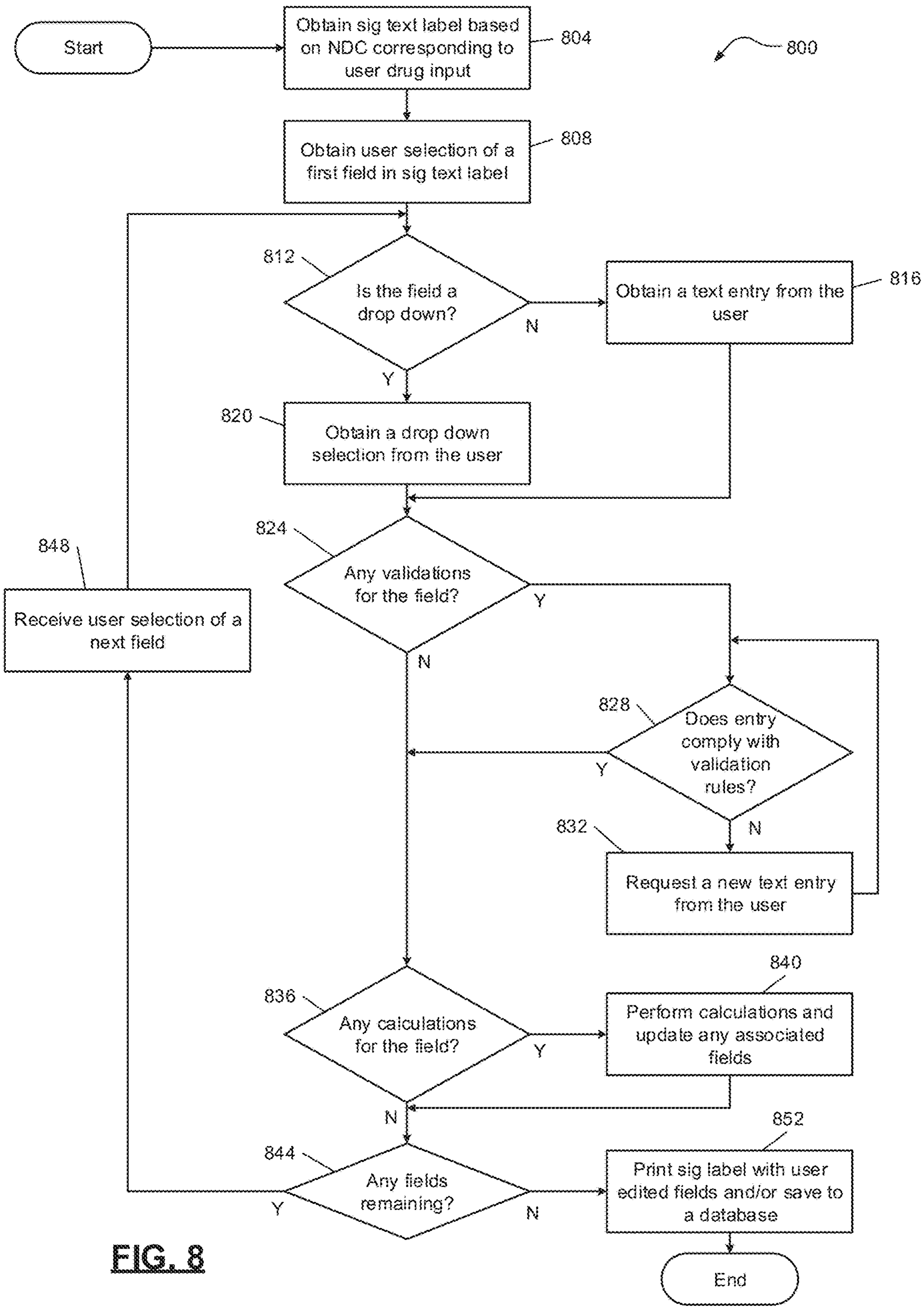
FIG. 8 is a flowchart depicting an example method of generating a sig text based on a user entry.

FIG. 8 is a flowchart depicting an example method 800 of an example method of generating a sig text based on a user entry. Although the example method 800 is described below with respect to the sig text builder system 400, the method 800 may be implemented in other processes, devices and/or systems.

At 804, control begins by obtaining a sig text label according to an NDC that corresponds to user drug input. For example, a user may enter a prescription drug and an NDC may be determined based on a lookup table associated with the prescription drug, a user may enter an NDC directly for the prescription to be filled, etc. Based on the NDC, a six text label may be obtained from a sig table database, such as the sig table database 402 of FIG. 4, and displayed to the user for dynamic editing.

At 808, control obtains a user selection of a first field in the sig text label. For example, the sig text label obtained from the sig text database may include multiple fields that can be edited by a user. The user may select a field that is first in sequential order within the label, in the middle or at end of the sig text label, etc.

Control determines at 812 whether the selected field is a drop-down field. If so, control proceeds to 820 to obtain a drop-down selection from the user. For example, once the user clicks on the drop-down menu field, a drop-down box may be displayed showing all available options, and the user may select the available options by clicking on the appropriate line of the drop-down box. Alternatively, if the selected the field selected by the user at 812 is not a drop-down field, control may proceeds to 816 to obtain a text entry from the user. For example, a text box may be displayed allows the user to enter their own text to supply the value for the selected sig text field.

After obtaining text from the user at 816, or obtaining a drop-down selection from the user at 820, control proceeds to 824 to determine whether any validations exist for the field. If so, control proceeds to 828 to determine whether the user entry complies with the validation rules. For example, a validation rule may specify upper or lower boundaries, ranges of input, etc., and control may determine whether user input is within the specified validation boundaries, ranges, etc. If not, control may proceed to 832 to display an error message and request a new text entry from the user. Control then determines again at 828 whether the new text entry from the user complies with the validation rules. Once the user has entered a value that complies with the validation rules (e.g., a value that is within the boundaries, within the acceptable ranges, etc.), control proceeds to 836.

At 836, control determines whether there are calculations associated with the field. For example, a field may include a calculated value based on other values of the sig text field, a field may be used to perform a calculation to determine the value of another field, etc. If the field is associated with any calculations, control proceeds to 840 to perform the calculations and update any associated fields. If the user enters a specified dosage value in the field, the dosage value may be used in a calculation for another field that determines the total amount of dosage for all doses based on a frequency, a calculation for another field may determine a permitted frequency based on the individual dose selected, etc. Once user enters a value in one field, control may then perform all calculations and update all other associated fields as appropriate.

After performing the calculations 840, or after control determines that the field is not associated with any calculations that 836, control proceeds to 844 to determine whether any fields remain in the sig text label. If so, control proceeds to 848 to receive a user selection of the next field in the same text label, and returns to 812 to receive the user entry regarding the field, and perform any appropriate validation rules, calculations, etc.

Once all fields have been edited by the user, and the user does not wish to make any further changes, control proceeds to 852 to print the sig text label and/or save the sig label to a record database. The printed sig label and/or saved record database sig label includes the fields as edited by the user. As mentioned above, the use of the sig builder process may increase efficiency for the user, reduce potential human error, provide increased consistency of labeling, allow for standardized data fields in a database for clinical monitoring, avoid redundant reentry of sig text to the database by a user, etc.

Figure 9A:
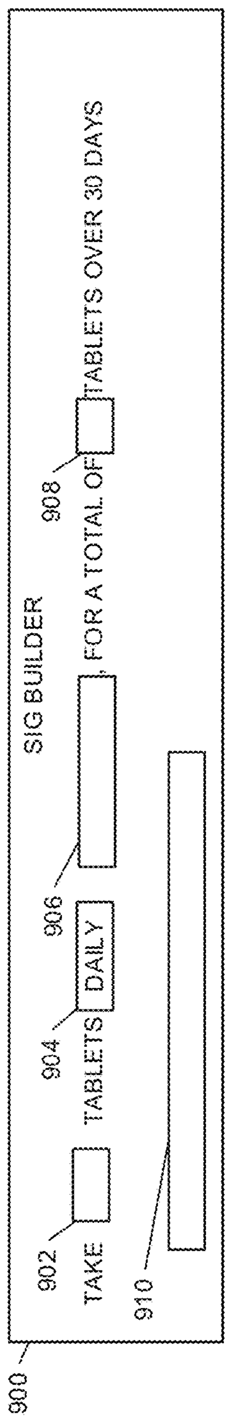
FIGS. 9A-9C illustrate example user interfaces for editing a sig text label.
Figure 9B:
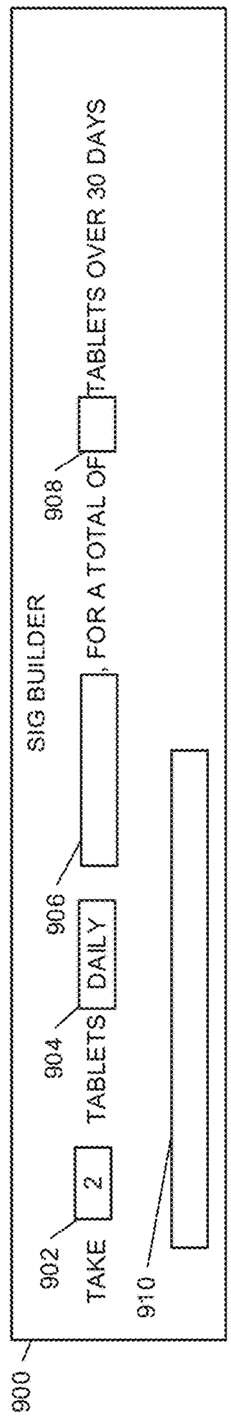
Figure 9C:
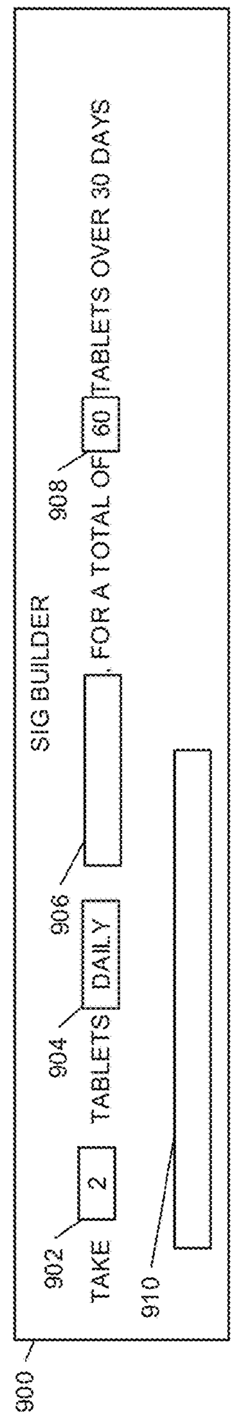

FIGS. 9A-9C illustrate an example process of a user editing fields of a sig text label 900. After the user provides an NDC, a sig text label that corresponds to the NDC may be presented to the user. In various implementations, the user may be able to select from among multiple "common" sig text labels that correspond to the provided NDC, a single sig text label may be presented that includes editable fields to modify different options that correspond to the NDC, the user may be able to bypass the sig builder to enter their own free text label, etc.

The sig text label 900 illustrated in FIG. 9A includes editable values fields 902 and 904, which allow the user to specify a dosage in the field 902 and a frequency in the field 904. The fields 902 and 904 may be text boxes for free text entry (which may include validation rules that limit the allowed values for the fields 902 and 904), may include drop down boxes that provide a limited choice of values for the user to pick from, etc.

The sig text label 900 also includes a calculated field 908 that calculates a total number of tablets based on the values entered in the fields 902 and 904, and two fields 906 that allow the user to enter additional text for the sig label if desired. For example, the user may add additional text within the default sig label at 906, or may add additional comments at the end of the default sig label at 910.

In FIG. 9B, the user has entered a value of two in the field 902, while leaving the field 904 as "Daily". The field 902 may have one or more validation rules, such as requiring the value to be an integer, requiring the value to be greater than zero but less than a number of tablets that would be harmful to a patient in all cases, etc. An error may be displayed within the label 900 if the user attempts to enter a value that is not allowed based on the validation rules.

As shown in FIG. 9C, the calculated field 908 is updated to display a total of sixty tablets over 30 days, based on the values in the fields 902 and 904. If the user were to change the value in the field 904 to another value, such as "twice a day", the field 908 may be updated to display a total of 120 tablets over 30 days.

CONCLUSION

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. The phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are IEEE Standard 802.15.4 (including the ZIGBEE standard from the ZigBee Alliance) and, from the Bluetooth Special Interest Group (SIG), the BLUETOOTH wireless networking standard (including Core Specification versions 3.0, 4.0, 4.1, 4.2, 5.0, and 5.1 from the Bluetooth SIG).

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module. For example, the client module may include a native or web application executing on a client device and in network communication with the server module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A computer system comprising:
- memory hardware configured to store instructions and a database; and
- processor hardware configured to execute the instructions, wherein the instructions include:
  - receiving input from a user, wherein the input is indicative of a specified national drug code (NDC);
  - querying the database to:
    - obtain a label text associated with the specified NDC,
    - obtain a field associated with the obtained label text, and
    - obtain a set of field options associated with the obtained field;
  - building a data structure including the obtained label text, the obtained field, and the obtained set of field options, including:
    - obtaining a set of text box fields associated with the obtained label text from the database query;
    - receiving a user text entry to the set of text box fields;
    - updating the set of text box fields to display the user text entry within the set of text box fields;
    - obtaining a field validation rule associated with the set of text box fields from the database query, wherein the field validation rule specifies upper and lower limits of ranges for the set of text box fields;
    - determining whether the user text entry to the set of text box fields satisfies the field validation rule; and
    - in response to a determination that the user text entry does not satisfy the field validation rule, displaying an error message and requesting a new text entry from the user;
  - converting the data structure to a dynamic web interface for displaying the obtained label text, the obtained field, and the obtained set of field options;
  - displaying, by the dynamic web interface, the obtained label text, the obtained field, and the obtained set of field options;
  - receiving a user selection of a field option of the obtained set of field options and updating the field to reflect the user selection;
  - generating, by a loading device, a printed label by printing the label text including the updated field,
  - applying, by the loading device, the printed label to a prescription container
  - moving, by the loading device, the labeled prescription container to a pallet or a puck; and
  - dispensing, by an automated dispensing device, a prescription drug into the labeled prescription container based on information associated with the printed label.

2. The computer system of claim 1 wherein the database includes:
- a label text table configured to store multiple label texts each associated with the NDC,
- a fields table configured to store multiple fields each associated with the label text, and a field options table configured to store multiple field option values each associated with the field.

3. The computer system of claim 1 wherein converting the data structure to the dynamic web interface includes performing a Hypertext Markup Language (HTML) conversion on the data structure to generate a dynamic web content user interface.

4. The computer system of claim 1 wherein the instructions include:

obtaining a calculated field associated with the obtained label text from the database query, wherein the calculated field includes a calculation algorithm; and in response to receiving the user text entry to the set of text box fields, performing the calculation algorithm to determine a value of the calculated field based on the user text entry, wherein:

the set of text box fields includes a dose option and a frequency option, the value of the calculated field includes a drug quantity for a user to at least one of consume, use, apply, or administer over a finite time period, and the calculation algorithm uses the dose option and the frequency option as inputs.

5. The computer system of claim 1 wherein:

querying the database to obtain the label text associated with the specified NDC includes obtaining a set of label texts associated with the specified NDC, and the instructions include:

displaying the set of label texts associated with the specified NDC to the user; and obtaining a user selection of a label text of the displayed set of label texts.

6. The computer system of claim 1 wherein the instructions include:

obtaining a hidden field associated with the obtained label text from the database query;

incorporating the hidden field in the data structure without displaying the hidden field in the web interface; and storing a value of the hidden field in the label text by saving the label text to a record database.

7. The computer system of claim 1 wherein the set of field options includes at least two of a dose option, a dosage unit option, or a frequency option.

8. The computer system of claim 1 wherein receiving the user selection of the field option of the obtained set of field options includes:

displaying the obtained set of field options as items in a drop-down menu of the web interface; and receiving a user selection of one of the items of the drop-down menu.

9. The computer system of claim 1 wherein the instructions include:

displaying a text entry box adjacent the obtained label text in the web interface;

receiving a user text entry to the text entry box; and updating the displayed label text to include the user text entry to the text entry box.

10. A computer-implemented method comprising:

receiving input from a user, wherein the input is indicative of a specified national drug code (NDC);

querying a database to:

obtain a label text associated with the specified NDC, obtain a field associated with the obtained label text, and obtain a set of field options associated with the obtained field;

building a data structure including the obtained label text, the obtained field, and the obtained set of field options, including:

obtaining a set of text box fields associated with the obtained label text from the database query;

receiving a user text entry to the set of text box fields;

updating the set of text box fields to display the user text entry within the set of text box fields;

obtaining a field validation rule associated with the set of text box fields from the database query, wherein the field validation rule specifies upper and lower limits of ranges for the set of text box fields;

determining whether the user text entry to the set of text box fields satisfies the field validation rule; and in response to a determination that the user text entry does not satisfy the field validation rule, displaying an error message and requesting a new text entry from the user;

converting the data structure to a dynamic web interface for displaying the obtained label text, the obtained field, and the obtained set of field options;

displaying, by the dynamic web interface, the obtained label text, the obtained field, and the obtained set of field options;

receiving a user selection of a field option of the obtained set of field options and updating the field to reflect the user selection;

generating, by a loading device, a printed label by printing the label text including the updated field;

applying, by the loading device, the printed label to a prescription container;

moving, by the loading device, the labeled prescription container to a pallet or a puck; and dispensing, by an automated dispensing device, a prescription drug into the labeled prescription container based on information associated with the printed label.

11. The method of claim 10 wherein converting the data structure to the dynamic web interface includes performing a Hypertext Markup Language (HTML) conversion on the data structure to generate a dynamic web content user interface.

12. The method of claim 10 further comprising:

obtaining a calculated field associated with the obtained label text from the database query, wherein the calculated field includes a calculation algorithm; and in response to receiving the user text entry to the set of text box fields, performing the calculation algorithm to determine a value of the calculated field based on the user text entry, wherein:

the set of text box fields includes a dose option and a frequency option, the value of the calculated field includes a drug quantity for a user to at least one of consume, use, apply, or administer over a finite time period, and the calculation algorithm uses the dose option and the frequency option as inputs.

13. The method of claim 10 wherein:

querying the database to obtain the label text associated with the specified NDC includes obtaining a set of label texts associated with the specified NDC, and the method further includes:

displaying the set of label texts associated with the specified NDC to the user; and obtaining a user selection of a label text of the displayed set of label texts.

14. The method of claim 10 further comprising:

obtaining a hidden field associated with the obtained label text from the database query;

incorporating the hidden field in the data structure without displaying the hidden field in the web interface; and storing a value of the hidden field in the label text by saving the label text to a record database.

15. The method of claim 10 wherein the set of field options includes at least two of a dose option, a dosage unit option, or a frequency option.

16. A non-transitory computer-readable medium comprising processor-executable instructions that include:

receiving input from a user, wherein the input is indicative of a specified national drug code (NDC);

querying a database to:

obtain a label text associated with the specified NDC, obtain a field associated with the obtained label text, and obtain a set of field options associated with the obtained field;

building a data structure including the obtained label text, the obtained field, and the obtained set of field options, including:

obtaining a set of text box fields associated with the obtained label text from the database query;

receiving a user text entry to the set of text box fields;

updating the set of text box fields to display the user text entry within the set of text box fields;

obtaining a field validation rule associated with the set of text box fields from the database query, wherein the field validation rule specifies upper and lower limits of ranges for the set of text box fields;

determining whether the user text entry to the set of text box fields satisfies the field validation rule; and in response to a determination that the user text entry does not satisfy the field validation rule, displaying an error message and requesting a new text entry from the user;

converting the data structure to a dynamic web interface for displaying the obtained label text, the obtained field, and the obtained set of field options;

displaying, by the dynamic web interface, the obtained label text, the obtained field, and the obtained set of field options;

receiving a user selection of a field option of the obtained set of field options and updating the field to reflect the user selection;

generating, by a loading device, a printed label by printing the label text including the updated field;

applying, by the loading device, the printed label to a prescription container;

moving, by the loading device, the labeled prescription container to a pallet or a puck; and dispensing, by an automated dispensing device, a prescription drug into the labeled prescription container based on information associated with the printed label.

* * * * *